United States Patent
Bar-Shavit

(10) Patent No.: US 6,183,954 B1
(45) Date of Patent: Feb. 6, 2001

(54) METHOD FOR EVALUATING THE METASTATIC TENDENCY OF TUMORS

(75) Inventor: Rachel Bar-Shavit, Jerusalem (IL)

(73) Assignee: Hadasit Medical Research Services and Development Company Ltd., Jerusalem (IR)

(*) Notice: Under 35 U.S.C. 154(b), the term of this patent shall be extended for 0 days.

(21) Appl. No.: 09/011,600
(22) PCT Filed: Aug. 8, 1996
(86) PCT No.: PCT/IL96/00077
  § 371 Date: Mar. 10, 1998
  § 102(e) Date: Mar. 10, 1998
(87) PCT Pub. No.: WO97/07387
  PCT Pub. Date: Feb. 27, 1997

(30) Foreign Application Priority Data

Aug. 10, 1995 (IL) .................................................. 114890

(51) Int. Cl.[7] .............................. C12Q 1/68; C12P 19/34; C07H 21/04
(52) U.S. Cl. ............................ 435/6; 435/91.2; 435/91.5; 435/91.51; 536/23.5
(58) Field of Search ........................... 435/6, 91.2, 91.51, 435/91.5; 536/24.31, 24.33, 23.5

(56) References Cited

U.S. PATENT DOCUMENTS

| | | | |
|---|---|---|---|
| 5,049,662 | * | 9/1991 | Steeg ..................................... 536/27 |
| 5,500,412 | | 3/1996 | Carney et al. ........................ 514/13 |
| 5,516,889 | | 5/1996 | Hollenberg ........................... 530/317 |

OTHER PUBLICATIONS

Wojtukiewicz et al., "Solid Tumor Cells Express Functional "Tethered Ligand"Thrombin Receptor", Cancer Research, Feb. 1995, vol. 55, pp. 698–704.

D. Walz et al., "The Role of Thrombin in Tumor Cell Metastasis", Invasion Metastasis, 1994–1995, vol. 14, pp. 303–308.

E. Yoshida et al., "Enhancement of the Expression of Urokinase–Type Plasminogen Activator from PC–3 Human Prostate Cancer Cells by Thrombin", Cancer Research, Jun. 1994, vol. 54, pp. 3300–3304.

E. Fisher et al., "Tissue Factor–Initiated Thrombin Generation Activates the Signaling Thrombin Receptor on Malignant Melanoma Cells", Cancer Research, Apr. 1995, vol. 55, pp. 1629–1632.

L. Brass et al., "Agonist Receptors and G Protein as mediators of Platelet Activation", In: Mechanisms of Platelet Activation and Control, Edited by Authi et al. New York: Plenum Press, 1993, pp. 17–36.

Ed Harlow et al., "Antibodies, A Laboratory Manual," Cold Spring Harbor Laboratory, 1988, pp. iii–ix.

David G. Wilkinson, "The theory and practice of *in situ* hybridization," A Practical Approach, pp. 1–11. (date not available).

"A Technique for Radiolabeling DNA Restriction Endonuclease Fragments to High Specific Activiy", Analytical Biochemistry, vol. 137, (1984), pp. 266–7..

(List continued on next page.)

Primary Examiner—Carla J. Myers
Assistant Examiner—Diana Johannsen
(74) Attorney, Agent, or Firm—Oliff & Berridge, PLC

(57) ABSTRACT

The present invention concerns a method for evaluating the metastatic tendency of tumor cells by determining the level of expression (mRNA level) of the gene coding for the thrombin receptor (ThR) or by determining the level of the thrombin receptor present on the membranes or within the tumor cells. A high level of either of the above indicates a high metastatic tendency, a low level indicates a low metastatic tendency and an intermediate level indicates a moderate metastatic tendency. The present invention further concerns a kit for use in the above method.

4 Claims, 8 Drawing Sheets

OTHER PUBLICATIONS

M. Culty et al., "Binding and Degradation of Hyaluronan by Human Breast Cancer Cell Lines Expressing Different Forms of CD44: Correlation with Invasive Potential," *Journal of Cellular Physiology*, vol. 160, (1994) pp. 275–286.

Thien–Khai H. Vu et al., "Molecular Cloning of a Functional Thrombin Receptor Reveals a Novel Proteolytic Mechanism of Receptor Activation," *Cell*, vol. 64, Mar. 22, 1991, pp. 1057–1068.

Erik W. Thompson et al., "Association of Increased Basement Membrane Invasiveness With Absence of Estrogen Receptor and Expression of Vimentin in Human Breast Cancer Cell Lines, " *Journal of Cellular Physiology* (1992), vol. 150, pp. 534–544.

Dennis J. Slamon et al., "Studies of the HER–2/*neu* Proto–oncogene in Human Breast and Ovarian Cancer," *Science*, vol. 244, May 12, 1989, pp. 707–712.

Michael F. Press et al., "Her–2/*neu* Expression in Node–negative Breast Cancer: Direct Tissue Quantitation by Computerized Image Analysis and Association of Overexpression with Increased Risk of Recurrent Disease," *Cancer Research*, vol. 53, Oct. 15, 1993, pp. 4960–4970.

Patricia J. McConahey et al., "Radioiodination of Proteins by the Use of the Chloramine–T Method," Radioimmunoassays and Immunoradiometric Assays, *Methods in Enzymology*, vo.1. 70, (1980), pp. 210–213.

* cited by examiner

METHOD FOR EVALUATING THE METASTATIC TENDENCY OF TUMORS

FIELD OF THE INVENTION

The present invention concerns a method for evaluating the metastatic tendency of tumor cells and a kit for use in said method.

BACKGROUND OF THE INVENTION

Metastasis is a multifactorial process by which tumor cells escape from the primary tumor disseminate through blood and lymph vessels evade host immune defence and home to specific target organs where they extravasate and re-colonize. Metastatic cells must encounter and cross the basement membrane during the extravasation of the blood vessels. The metastatic process is usually described as a three-step model, wherein metastatic cells must first adhere to the basement membrane, then digest via proteolytic enzymes the basal lamina, and finally migrate through the vessel wall.

Evaluating the metastatic potential of a specific tumor is essential for diagnostic and prognostic purposes, for determining optimal course of treatment as well as for various research purposes such as developing therapeutical methods and medicaments for the treatment of metastasis.

Correlation between various biomolecules and the metastatic tendency of tumor cells has been previously described. There has been a disclosure of association of increased basement membrane invasiveness, which is the first step in the process of metastasis, with the absence of estrogen receptor and expression of vimentin in a human breast cancer cell line (Thompson et al, *J. of Cellular Plzysiol.*, 150:534–544 (1992)). A correlation between the invasive potential of various human breast cancer cell lines and binding and degradation of hyaluronan has also been described (Cultry et al., *J. of Cellular Physiol.*, 160:275–286 (1994)). Metastatic potential of various tumor cell lines has also been associated with amplification in the expression of various proto-oncogenes, such as the HER-2/neu proto-oncogene which is amplified in 25% of human primary breast cancer and its amplification is associated with shorter time to relapse and shorter overall survival (Slamon et al., *Science*, 244:707–712 (1989)).

Although currently change in the level of some of the above biomolecules, especially amplification of the HER-2/neu proto-oncogenes, is used for prognostic purposes, the prognostic use of expression or amplification of this gene has been quite controversial (Press, M. F. et al, *Cancer Res*, 53:4960–4970 (1993)). The prognostic factors currently used to assess the breast tumor state are: tumor size, histological grade, steroid hormone receptor status, DNA ploidy, proliferative index, cathepsin D and analysis of growth factor receptors such as epidermal growth factor receptor.

There is a great need today for additional, accurate prognostic factors for tumor cells which will be easy to identify and which are in good correlation to the metastatic tendency of those cells.

The thrombin receptor (ThR) has been cloned and identified as a member of the seven trans-membrane domain super-family of G-protein coupled receptors. It is activated by cleavage of the $Arg^{41}$-$Ser^{42}$ residues of the extracellular N-terminus part of the receptor by the protease thrombin. This cleavage exposes the ligand of the thrombin receptor which is an integral part of the receptor itself. Thus, the ThR serves as a classical substrate for protease, rather than the traditional ligand-receptor complex, during the course of cellular activation (Vu, et al., *Cell*, 64:1057–1068, (1991)). Recently, there has been a report that W256 carcinoma and mouse melanoma tumor cells contain functional thrombin receptors (Wojtukiewicz, et al, *Cancer Res.*, 55:698–704 (1995)), however, only the existence and function of the thrombin receptor has been assessed in this publication and there has been no determination of the level of its expression, nor its connection to the malignancy of the tumor.

SUMMARY OF THE INVENTION

The present invention is based on the surprising finding that there exists a direct correlation between the level of ThR expression in tumor cells and their metastatic tendencies, so that high levels of ThR expression are evident in aggressive metastatic tumor cells, low to moderate levels of expression can be detected in medium metastatic tumor cells and essentially no detectable expression of ThR is evident in non-metastatic tumor cells.

The above surprising finding enables to evaluate the metastatic tendency of tumor cells by determining the level of ThR expression therein.

Thus, the present invention provides a method for evaluating the metastatic tendency of tumor cells comprising:
  (a) determining a test level of a cellular parameter in said cells said level of parameter being:
    (aa) the level of thrombin receptor (ThR), or
    (ab) the level of expression of a gene coding for ThR;
  (b) comparing said test level with a control level, being a level of a corresponding parameter obtained from a cell having a known metastatic tendency, a high or low test level indicating a high or low metastatic tendency, respectively.

The term "metastatic tendency" refers to the expressed metastatic capacity of tumors which have already begun their metastatic spread and begun recolonization in target organs, as well as to the future metastatic potential of tumors which are still in the initial pre-metastatic stage and which may metastasize in the future. A high metastatic tendency refers to a situation where the tumor cells metastasize rapidly and colonialize in many target sites. Moderate metastatic tendency refers to tumor cells which metastasize slowly, and colonialize only at a few target sites, and low metastatic tendency refers to tumor cells which virtually do not metastasize and are confined to their original site.

The tumor cells which metastatic tendency is evaluated can be any type of tumor cells, especially those types which feature varying levels of metastatic tendencies such as breast cancer, testicle cancer, melanoma, epithelial carcinoma, colon carcinoma, ovarian carcinoma, cervical carcinoma, as well as various types of sarcoma.

The level of ThR can be determined either by assaying the level expression of the gene coding for the thrombin receptor, i.e. by determining the mRNA level, or by determining directly the level of the thrombin receptor present either on the membranes of the cells or within the cytoplasm.

The levels of the mRNA can be determined. for example, by separating the mRNA molecules, obtained from the assayed cells. on an electrophoretogram (Northern blot) and then identifying the separated thrombin mRNA by hybridization with suitable probes which carry detectable labels; by in situ hybridization to the mRNA, present in the isolated tumor cell or present in isolated tissue obtained from the tumor, with suitable probes carrying detectable labels; or by RT-PCR amplification using suitable primers.

The ThR level may be determined for receptors present on the membrane of the tumor cells and/or present within the cell. The determination can be carried out, for example, by using antibodies capable of recognizing the thrombin receptor (either in its membranal or cytoplasmal forms, or in both forms) in one of the state-of-the-art immunoassays, or by determining the level of binding of a labeled ligand to the thrombin receptor.

Once the level of the thrombin receptor is determined, either through mRNA or through protein determination, it should be compared to the corresponding level of either mRNA or thrombin receptor of other cells which metastatic tendency is a priori known, which cells may also be non-tumor normal cells, or tumor cells from established cell lines known to have a high, low, or moderate metastatic tendency.

In practice and during clinical use there will be no need to calibrate de novo each ThR level obtained since it will already be known by the practitioner, due to prior experience which specific color pattern of an in situ hybridization, unique pattern of band formation in Western or Northern blot, or specific amount of mRNA amplified using RT-PCR, indicates that the ThR level is high and thus that the tumor cell features a high metastatic tendency. It is also possible to compare the levels obtained from the tested tumor cells to two corresponding control levels: one obtained from highly metastatic cell lines, and the other obtained from low metastatic cell lines to determine more precisely whether the tested level is high, low or intermediate.

Cells, which after being compared as specified above show a high level of ThR, are those which feature a high metastatic tendency; cells which show a low or almost no level of ThR are those which have low metastatic tendency; and cells which show intermediate levels are those which are usually moderately metastatic.

The present invention also concerns a kit for use in the above method.

Where the determination of the level of ThR is carried out by determining the level of mRNA, the kit may comprise labeled probes and reagents suitable for in situ hybridization, labeled probes and reagents for carrying out Northern blot, or reagents and primers necessary for RT-PCR.

Where the determination of the ThR is carried out by determining the level of the thrombin receptor, the kit may comprise antibodies capable of specifically binding to the ThR, either when present on the membranal surfaces of the tumor cells or when present within the cells, together with reagents for carrying out a suitable immunoassay. Alternatively, the kit for determining the ThR protein level may be based on a ligand-binding assay and in that case the kit should comprise a labeled ligand, which can be for example the synthetic peptide corresponding to residues $Ser^{42}$-$Lys^{51}$ of the native thrombin receptor (the so called "inner ligand").

The invention will now be further illustrated with reference to some specific non-limiting drawings and embodiments.

DETAILED DESCRIPTION OF THE INVENTION

I. Preparation of Probes Used in Northern Blot and in situ Hybridization (a) Method A 250 base pair fragment of thrombin receptor was obtained by PCR using as primer the following sequences derived from the human thrombin receptors:

```
Primer 1(SEQ ID NO:1):  5' ATGGAATTCTGCCACCTTAGATCC
Primer 2(SEQ ID NO:2):  5' ATGGGATGCGGAGGCTGACTACAA
```

The 250 b.p. fragments were shown by nucleotide sequence analysis to be the internal part of the cloned thrombin-receptor (ThR), nucleotides: 329–575 (according to Vu et al., Cell 64:1057–1068), including the internal ligand region peptide and sequences beyond (i.e. SEQ ID No: 3 SFLLRNPNDKYEPFWEDEEKNESGLTEY-RLVSINKSSPLQKQLPAFIS EDASGYLTSSWLTLFVPSVYTGVFVVSLP). The length of the fragment was determined by electrophoresis on 1% agarose gel in TAE (0.04M Tris-acetate, 0.001M EDTA) buffer.

Figure 2:
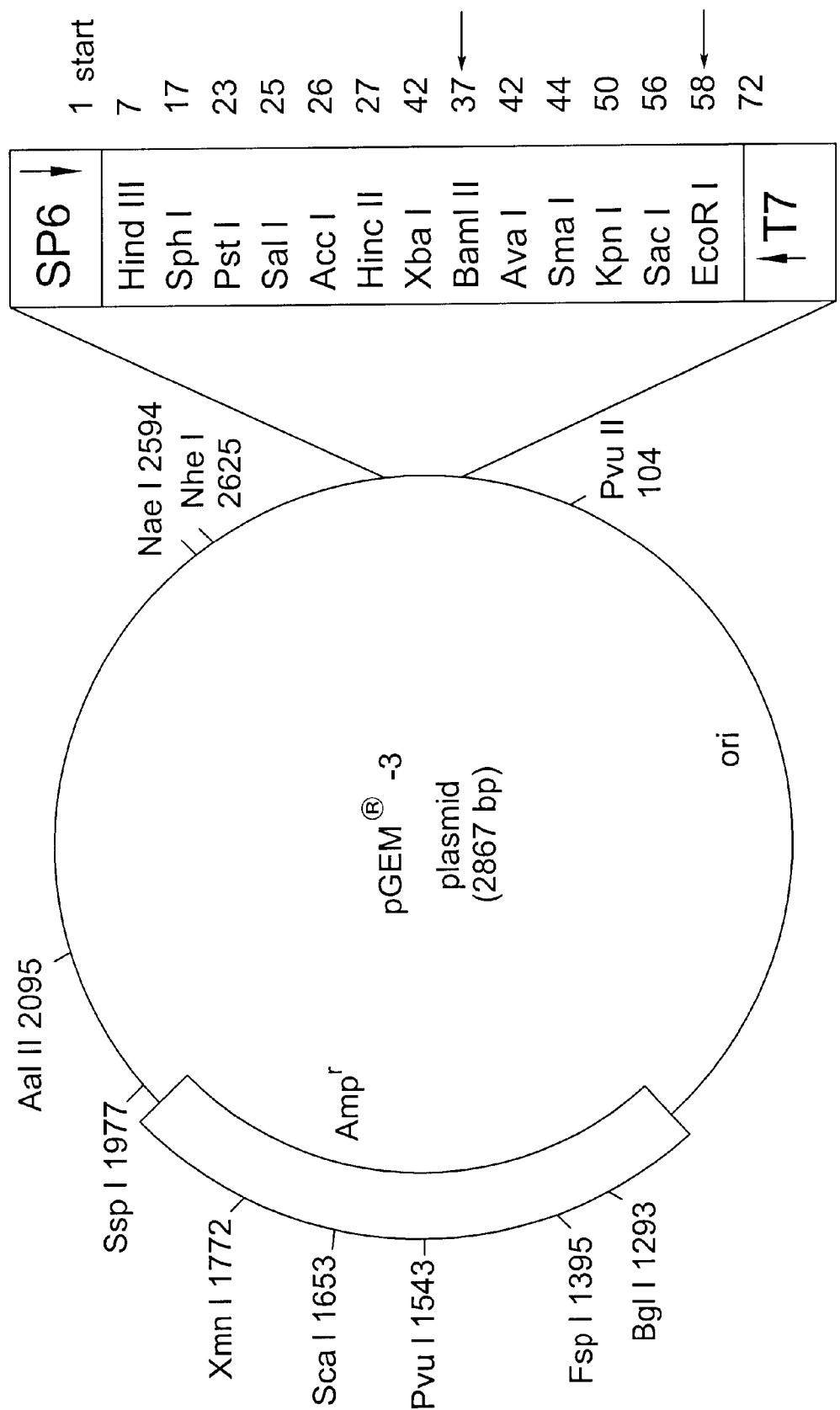
FIG. 2—pGEM-vector restriction map, the human ThR 250 base pair fragment inserted into the pGEM-vector at sites BamH1 and ECOR1 restriction enzymes; (the size of the pGEM-3 vector is 2867 b.p., sequence reference points: 1-SP6 RNA polymerase transcription; 72-T7 RNA polymerase transcription initiation site; 2851–2868—SP6 RNA polymerase promotor; 73.89—T7 RNA polymerase promotor; 7.63—multiple cloning sites; 100.158 lac operon sequences; 1100–1960—β-lactomase coding region).

The 250 b.p. fragments were inserted into a pGEM vector at sites of BamH1 and ECOR1 restriction enzymes, and the pGEM restriction map is shown in FIG. 2.

Bacteria (E.coli strain DH5) were transformed with said vector and grown in large quantities. The plasmid was isolated by the Wizard(™) Maxi prep (DNA Purification System, USA). The 250 b.p. fragment was isolated from the plasmid by digestion with the restriction enzymes: ECOR1 and BamH1 (Boehringer Mannheim, Mannheim Germany). The purified fragment, purified either by ethanol precipitation of Geneclean procedure, using Geneclean II kit, B10, (101 Joshua Way, Vista Calif. 92083), was labeled (according to Feinberg, A. P. and Vogelstein. B., Anal.

Biochem., 137:266, 1984) by using the random prime labeling of [α-$^{32}$P]-dCTP (kit from Boehringer-Mannheim, Cat. 1004760. Mannheim Germany).

Riboprobes were prepared by using the RNA Color Kit for non-radioactive in situ hybridization (RNP3300; Amersham. Buckinghamshire. England). For this, the plasmid (pGEM-3) was linearized by digestion with ECOR1 for the source of RNA polymerase (using the SP6 promoter present in pGEM-3). In parallel, digestion with BamH1 was performed and linearized DNA was used as a source for the T7 RNA polymerase (present in the pGEM-3 plasmid). Both linearized DNA were incubated, according to the manufacturer's instructions, with their appropriate RNA polymerase (either SP6 or T7) and with nucleotides and transcription reaction (Wilkinson, D. G., in "In-situ Hybridization: A practical approach", Ed. D. G. Wilkinson, IRL Press, Oxford pp. 1–14, 1992; Brunnings, S. et al, "In-Situ Hybridization: A Guide to radioactive and Non-radioactive In-Situ Hybridization Systems", Amersham International Amersham, 1993). Fluorescein-11-UTP incorporation during the transcription reaction determined the extent of synthesis.

Riboprobes at both directions: antisense, prepared using 7 SP6 promoter, and sense prepared using the T7 promoter which was used as a control, were added to paraffin embedded slides following appropriate deparaffinization step. Detection of the specifically hybridized mRNA was evaluated following appropriate blocking and addition of alkaline phosphatase conjugated antibody for 1 h at room temperature, developed in the presence of NBT and BCIP as substrates, in appropriate detection buffer.

(b) Results

Figure 1:
FIG. 1—a DNA electrophoretogram, lane A: 250 base pair fragment of human ThR DNA obtained by using RT-PCR human umbilical endothelial cells as a source; lanes B, C: same reaction of lane A with no DNA; lane D: molecular weight markers.

The ThR DNA obtained by PCR amplification was separated on a 1% gel agarose electrophoresis in TAE (0.04M Tris-acetate, 0.001M EDTA) buffer and the separation results are shown in FIG. 1, wherein lane A is the above 250 b.p. fragment; lanes B, C are the same reaction as described above with no DNA present; and lane D is Molecular Weight Markers which verified the size of the PCR obtained probe.

II. Level of ThR Expression in Three Epithelial Carcinoma Cell-lines of Differential Metastatic Potential

1. RNA Determination (a) Method

Three epithelial carcinoma cell lines were used: MCF-7, characterized as an epithelial carcinoma with minimal aggressive properties which grows in nude mice without Matrigel but does not metastasize even in the presence of Matrigel; MDA 231 which is a moderately aggressive carcinoma which does not grow without Matrigel in nude mice but grows with moderate amounts of Matrigel; MDA 435 which is a very aggressive carcinoma which grows with wide-spread metastasis in nude mice even in the absence of Matrigel.

20 μg/lane of RNA were obtained from the above three carcinoma lines and were separated on a 1.5% agarose/formaldehyde gel. The 250 b.p. ThR DNA label with [α-$^{32}$P] dCTP obtained as described in Example I above was used as the hybridization probe for the separated mRNA.

(b) Results

Figure 3:
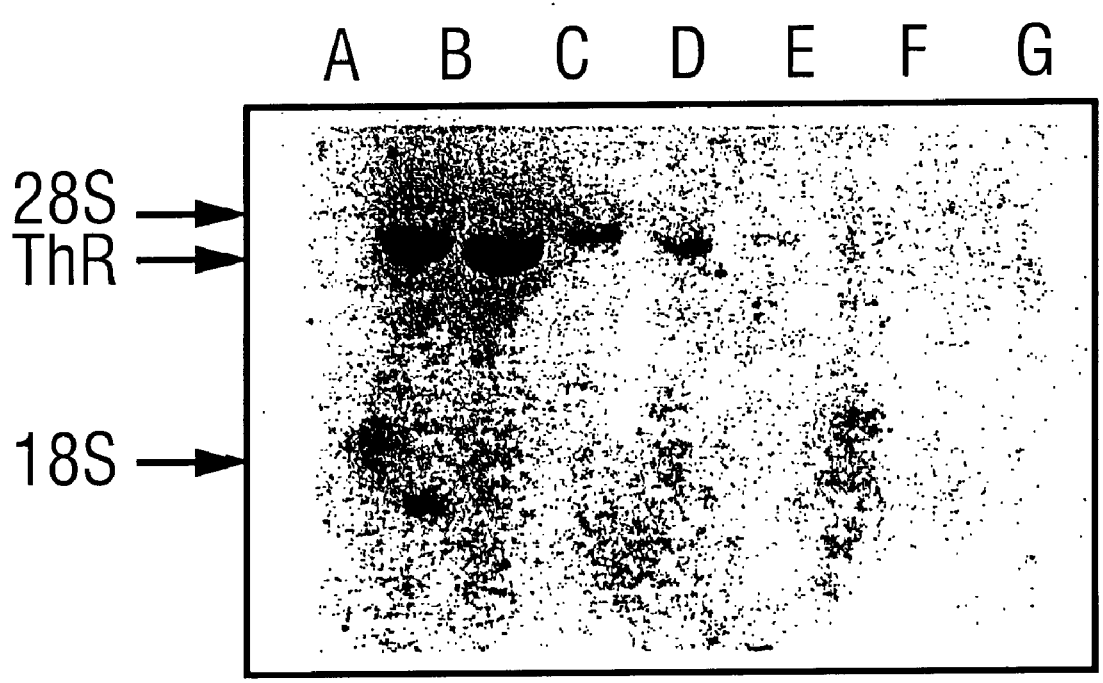
FIG. 3—electrophoretogram of ThR mRNA obtained from various human breast cell lines; lanes A, B: MDA 435; lanes C.D,E: MDA 231; lanes F, G: MCF-7.

The results are shown in FIG. 3, wherein lanes A and B are the results with the highly metastatic cell line MDA 435; lanes C, D and E are results with the moderately metastatic cell line MDA 231 and lanes F and G are the results with the low metastatic cell line MCF-7.

As can be seen, the highly metastatic cell line expressed large amounts of ThR mRNA, the moderately metastatic cell line expressed intermediate amounts of ThR mRNA and the non-metastatic cell lines expressed essentially no ThR mRNA.

In order to ensure that the total amounts of mRNA in all three cell lines were essentially the same, the amounts of β-actin mRNA was also determined and was found to be about the same in all three cells lines (Data not shown).

2. Protein Determination (a) Method

The highly metastatic MDA 435 cell line and the non-metastatic MCF-7 cell line were used. Lysates of cells were prepared and either 200 μg/lanes (lanes A.C.E) or 100 μg/lanes (lanes B,D,F) were applied for separation on SDS-Phase together with molecular weight markers.

(b) Results

Figure 6:
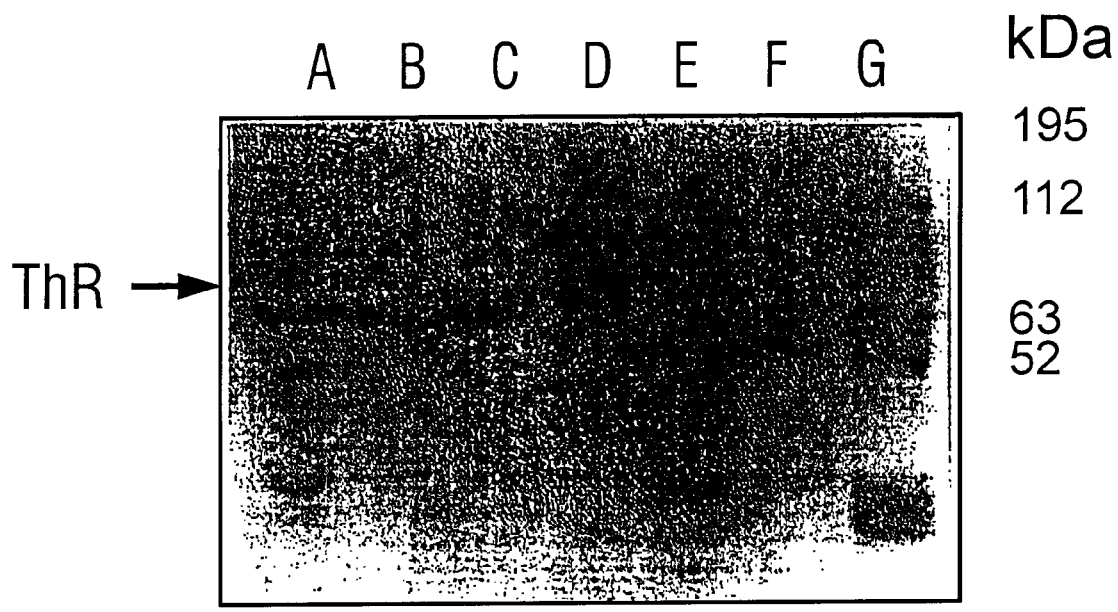
FIG. 6—Western blot of cell lines expressing ThR (lanes A–D), and cell lines which do not express ThR (lanes E and F); lane G Molecular Weight Markers.

The results are shown in FIG. 6. As can be seen, lanes of cell lines which are highly metastatic (lanes A–D) show a high level of ThR protein while lanes which are not metastatic show essentially no expression of ThR (lanes E,F).

III. ThR Expression Detected by in situ Hybridization with Metastatic and non-metastatic Epithelial Carcinoma Cell Lines (a) Method The data obtained in Example II above concerning the amounts of mRNA ThR in various carcinoma cell lines determined by Northern blot was confirmed by in situ hybridization analysis of the MDA 435 and MCF-7 cell lines monolayers using both sense and antisense riboprobes of ThR obtained as described in Example I.

The cell monolayers were fixed for 10 min in ethanol, hydrated sequentially by 5 min incubations in 70% ethanol, 50% ethanol and 30% ethanol. Then, 10 min incubation in 5 mM MgCl$_2$ followed by treatment of the cells with 0.02N HCl for 10 min, and washes in 5 mM EDTA in 2×SSC (50'C., 30 min). No proteinase K treatment was performed on the cell monolayers. Finally, cells were treated with 4% formaldehyde (25 min) followed by 2 washes in 5 mM MgCl$_2$. Linearized plasmid with the relevant enzyme (estimated ~600 ng) were used for riboprobe synthesis (estimated ~20 ng/well) incubated overnight at 55° C. with the cell monolayers.

(b) Results

Figure 4:
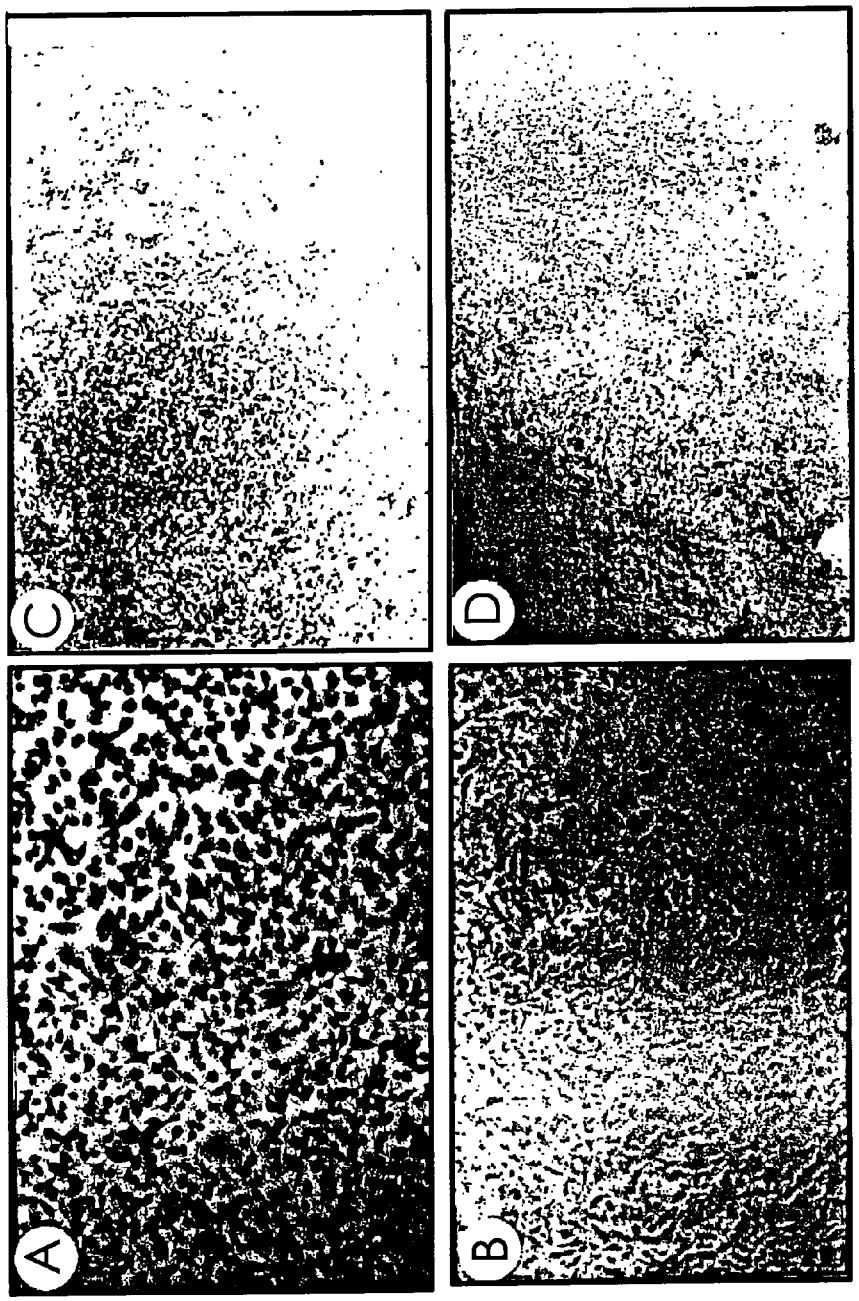
FIG. 4—in situ hybridization of antisense (A,C) or sense (B,D) mRNA probes to human breast cancer cell lines having no metastatic potential MCF-7 (C,D) or high metastatic potential MDA 231 (A,B)

The results are shown in FIG. 4 were the antisense direction of the riboprobes is depicted in pictures A and C and sense riboprobes in pictures B and D. The cell lines used were either the non-metastatic MCF-7 (pictures C and D) or the highly metastatic MDA 435 cells (pictures A and B).

As can be seen, no hybridization was detected in MCF-7 cells, while strong and abundant distribution of the probe was present in the aggressive metastatic cells.

IV. In situ Hybridization of Paraffin-embedded Breast Tumors

In situ hybridization with the above riboprobes was also carried out for paraffin-embedded breast tumors of patients with highly invasive metastasis and patients with a primary tumor with no seemingly metastatic spread. For this, hybridization using digoxigenin (fluorescein-11)-UTP RNA color kit (Amersham, RPN 3300) was employed. Preliminary data show specific staining of the carcinoma cells of patients with metastasis, i.e. positive staining with the antisense riboprobe obtained by the SP6 promotor and no staining with the sense riboprobe obtained by the T7 promotor, as well as positive staining around vessel walls throughout the breast section. Patients with no metastasis, exhibited no detectable staining

V. Anti-human ThR Antibodies (a) Method of Preparation

A synthetic peptide corresponding to residues $Ser^{42}$-$Lys^{51}$ of the native thrombin (SEQ ID No: 4S-F-L-L-R-N-P-N-D-K) was used to immunize a rabbit by a subcutaneous co-injection with Complete Freund's Adjuvant (1:1 ratio) for the first injection, then 2–3 weeks later another injection of the peptide, conjugated to KLH with incomplete Freund's Adjuvant (according to Antibodies. A Laboratory Manual by Ed Harlow and David Lane, Cold Spring Harbor Laboratory, 1988). The immune serum thus obtained was affinity purified for antibodies using the above synthetic peptide.

5 μg/lane of the above synthetic peptide were used to coat ELISA plates and the serum obtained from the rabbit as described above was analyzed for specificity by adding serial dilutions of antibody (2–16 h, 4° C.), followed by 3 washes and sequential incubation at 24° C. for 1 h with alkaline phosphatase conjugated anti-rabbit antibodies (Promega; Hollow Road, Madison, Wis., USA) added at a dilution of 1:5000. The wells were then washed three times and the substrate nitrophenyl phosphate (PNPP) in diethanolamine buffer was added. Positive reaction was evaluated by the color development at O.D. 405 nm.

(b) Results

Figure 5:
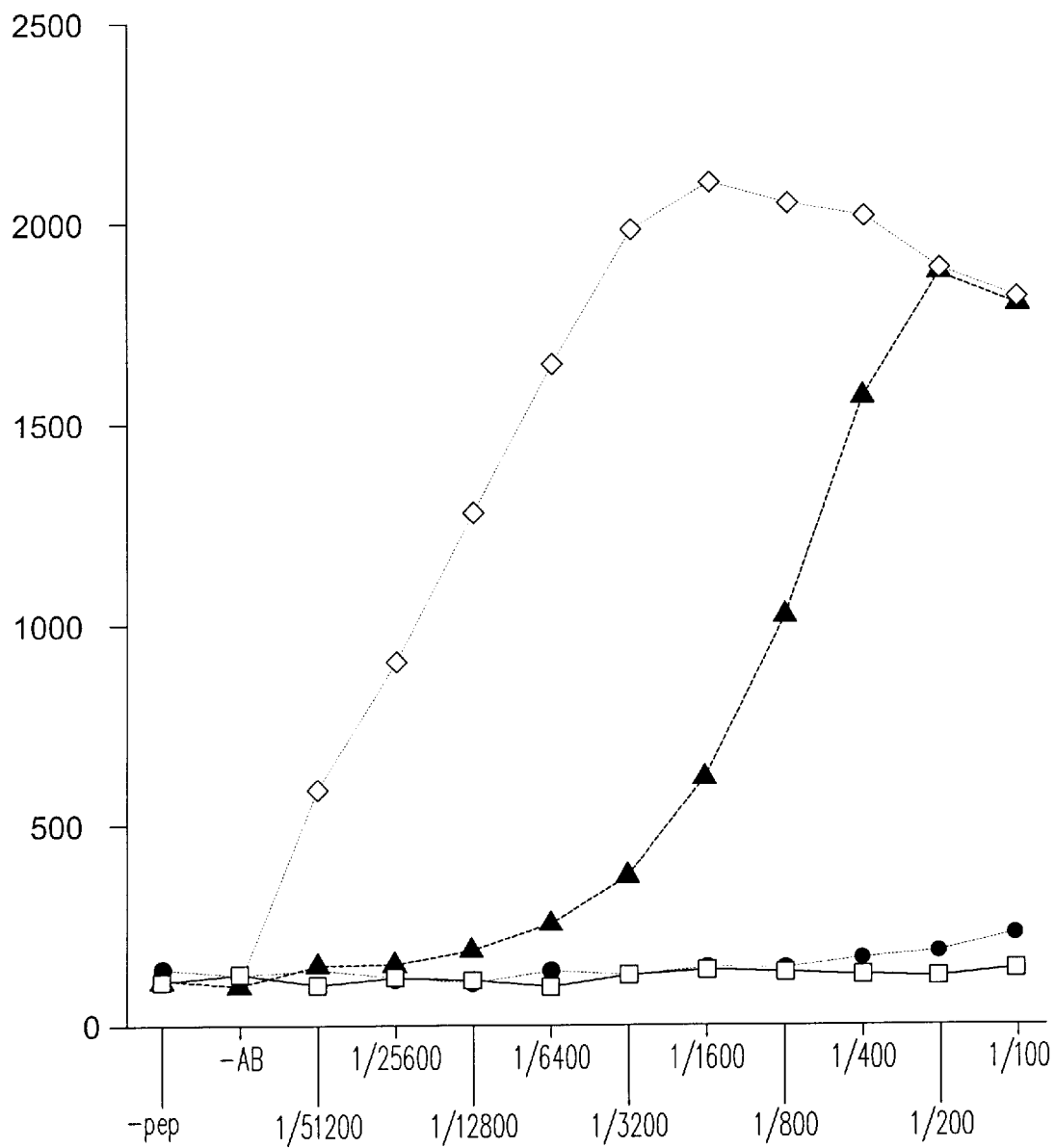
FIG. 5—binding of anti-ThR antibodies to the N-terminal residue $Ser^{42}$-$Lys^{51}$ of human ThR, determined by ELISA (SIH AB-antibodies against human ThR; SIH WR-white rabbit; pre-SIH pre-immune serum of white rabbit; BR black rabbit)

As can be seen in FIG. 5, serum of immunized animal SIH WR 2318 (◇) and SH BR 2318 (●) was able to specifically bind to the synthetic peptide as compared to serum of unimmunized animal SIH W pre (□) and SIH BR pre (▲) which showed no specific binding.

VI. Identifying the Level of ThR Protein Using a Ligand-binding Assay (a) Method of Preparation of Labeled Ligands A synthetic 14 amino acid polypeptide which corresponds to the internal thrombin receptor ligand was radiolabeled. Radiolabeling of the 14 amino acid peptide (SEQ ID No: 5:S-F-L-L-R-N-P-N-D-K-Y-E-P-F) was performed using chloramine T. as previously described (McConahay, P. J. et al., *Method Enzymol.*, 70:210 (1980)). Briefly. 10 μg of the peptide was added to 60 μl of 0.2 M sodium phosphate, pH 7.2, containing 1 μCi $Na^{125}I$. Chloramine T (10 μl of 1 mg/ml) was added for 45 seconds at room temperature and the reaction was stopped by the addition of 50 μl 0.05% sodium metabisulfite and 50 μl of 10 mM KI. The reaction mixture was then applied on to a Sephadex G-10 column. Fractions were collected in phosphate buffer (0.1M, pH 7.2). The specific activity was $0.8–1.1×10^5$ cpm/ng peptide and the labeled material was kept for up to 4 weeks at −70° C.

(b) Method of Binding and Crosslinking of the Labeled Peptides to Smooth Muscle Cells (SMC)

SMC cells were used as a model of cells carrying the ThR which can be detected by binding a labeled ligand prepared as described in (VIa) above.

$5×10^5$ Cells/well were grown to confluence in 60 mm culture wells. Confluent cultures were transferred to 4° C., washed once with PBS and incubated for 2 h with various concentrations of $^{125}I$-peptide in the absence or presence of 1000 fold excess unlabeled peptide. The cultures were washed three times with PBS, followed by incubation for 30 min at 24° C. with the bifunctional cross-linker disuccinimidyl suberate (DSS; 4 mM) in DMEM containing 0.2% BSA. At the end of this incubation, cells were washed and dissolved in SDS-PAGE sample buffer for analysis by SDS-PAGE.

(c) Results

Figure 7:
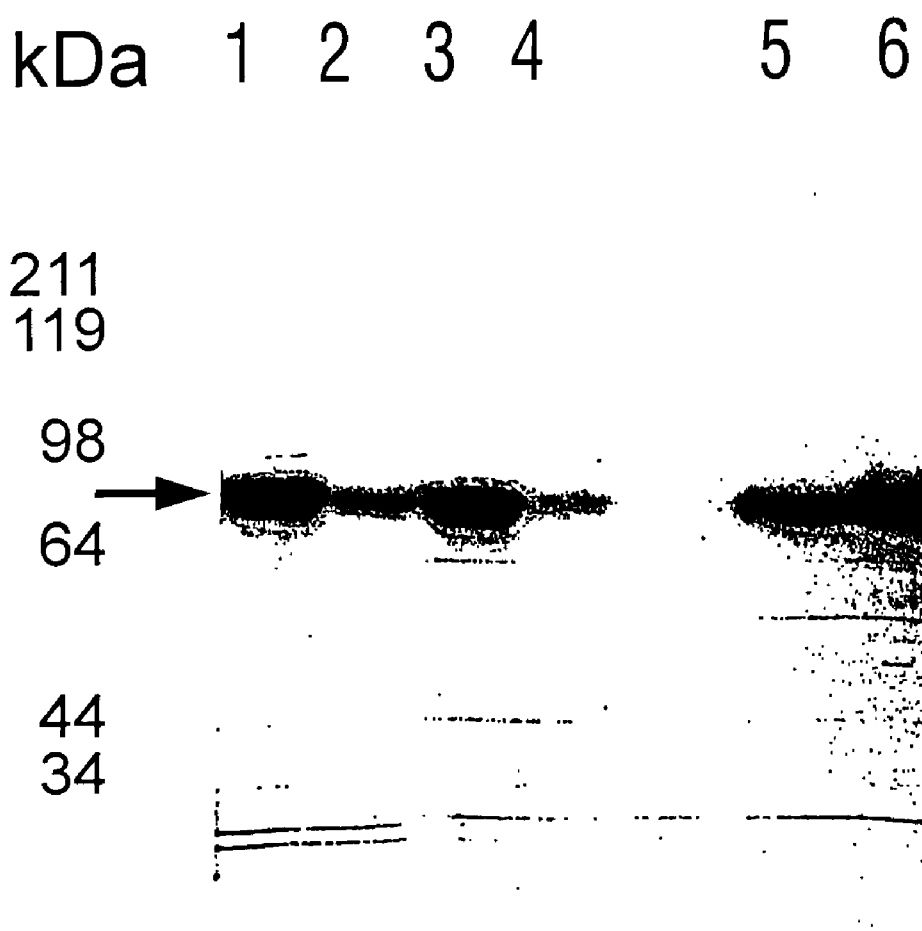
FIG. 7—SDS-PAGE of $^{125}$I-thrombin receptor agonist peptide to SMC: (lanes 1,2: untreated cells; lanes 3,4: cells pre-treated with heparinase; lanes 5,6: cells treated with chondrotirase ABC; lanes 2,4,5: cells in the presence of labeled ligand; lanes 1,3,6: cells in the absence of labeled ligand).

As can be seen in FIG. 7, the complex of the ThR and the labeled ligand (lanes 2,4,5) having a molecular weight of about 70 kDa could be detected as compared to ThR with no ligands (lanes 1,3,6) showing that the ligand-binding assay is valid for detecting ThR.

VII. The Level of ThR as Determined by RT-PCR (a) Method

Different amounts of RNA (2.5, 5 and 10 μg/reaction) of the three cell lines: MCF-7, MDA-231 and MDA-435, respectively, were used to prepare cDNA. One-tenth (5 μl out of 50 μl total reaction mixture) of the cDNA formed was further used for PCR amplification in the presence of the ThR-primers. The PCR products were separated on 1% agarose gel in TAE buffer.

(b) Results

Figure 8:
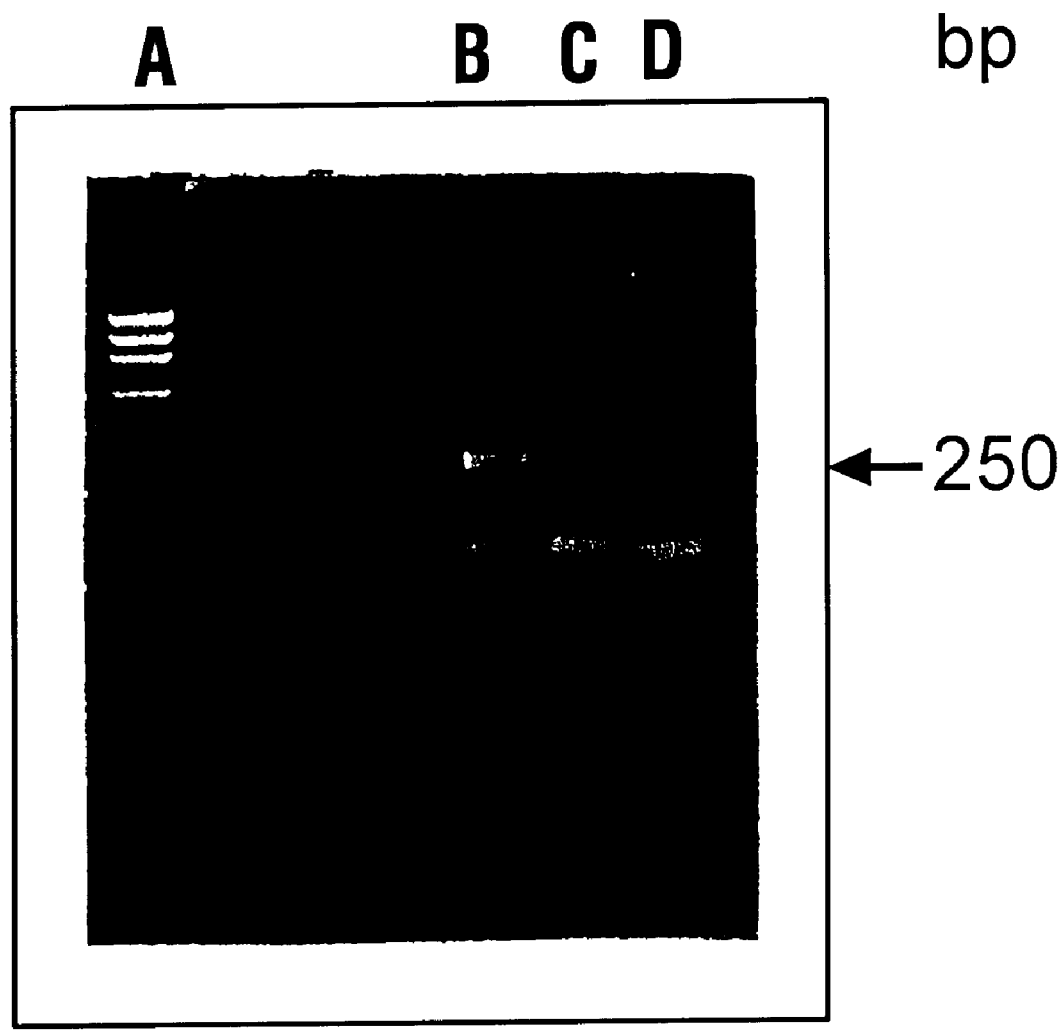
FIG. 8—the level of ThR as determined by RT-PCR.

As can be seen in FIG. 8 at none of the concentrations used a distinct band product of ThR could be observed for the non-metastatic MCF-7 cells. The highly metastatic MDA-231 cells showed a high level of ThR at all concentrations used, while the moderately metastatic MDA-435 showed a distinct band but only at the high concentrations of 5 and 10 μg/reaction.

---

What is claimed is:

1. A method for determining whether the metastatic tendency of tumor cells is high or low, said method comprising:
   (a) (quantitating the level of thrombin receptor (ThR) mRNA in said tumor cells; and
   (b) comparing said level with a control level, said control level being a level of ThR mRNA from a cell known to have a high metastatic tendency or a cell known to have a low metastatic tendency, a high or low level of the ThR mRNA in the tumor cells as determined by said comparison indicating a high or low metastatic tendency of the tumor cells, respectively.

2. A method according to claim 1, wherein quantitating the level of ThR mRNA comprises:
   (i) obtaining mRNA from the tumor cells;
   (ii) separating the mRNA by size on an electrophoretogram;
   (iii) applying on to said electrophoretogram probes carrying a detectable label which specifically hybridize with ThR mRNA; and
   (iv) quantitating the level of label on the electrophoretogram, wherein said level of label is indicative of the level of ThR mRNA.

3. A method according to claim 1, wherein quantitating the level of ThR mRNA comprises hybridization in situ of said tumor cells with probes carrying a detectable label, which probes specifically hybridize with the ThR mRNA, and quantitating the level of label attached to said tumor cells, wherein said level of label is indicative of the level of ThR mRNA.

4. A method according to claim 1, wherein quantitating the level of ThR mRNA comprises:
   (i) synthesis by reverse transcription of cDNA wherein the ThR mRNA serves as a template;
   (ii) amplification by polymerase chain reaction (PCR) of the cDNA; and
   (iii) quantitating the level of the amplified cDNA, wherein said level is indicative of the level of ThR mRNA.

* * * * *

SEQUENCE LISTING (1) GENERAL INFORMATION:

(iii) NUMBER OF SEQUENCES: 5

(2) INFORMATION FOR SEQ ID NO:1:

(i) SEQUENCE CHARACTERISTICS:
      (A) LENGTH: 24 base pairs
      (B) TYPE: nucleic acid
      (C) STRANDEDNESS: single
      (D) TOPOLOGY: linear (ii) MOLECULE TYPE: DNA (genomic)

(xi) SEQUENCE DESCRIPTION: SEQ ID NO:1:

ATGGAATTCT GCCACCTTAG ATCC          24

```
(2) INFORMATION FOR SEQ ID NO:2:

(i) SEQUENCE CHARACTERISTICS:
        (A) LENGTH: 24 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:2:

ATGGGATGCG GAGGCTGACT ACAA                                              24

(2) INFORMATION FOR SEQ ID NO:3:

(i) SEQUENCE CHARACTERISTICS:
        (A) LENGTH: 77 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:3:

Ser Phe Leu Leu Arg Asn Pro Asn Asp Lys Tyr Glu Pro Phe Trp Glu
1               5                   10                  15

Asp Glu Glu Lys Asn Glu Ser Gly Leu Thr Glu Tyr Arg Leu Val Ser
            20                  25                  30

Ile Asn Lys Ser Ser Pro Leu Gln Lys Gln Leu Pro Ala Phe Ile Ser
        35                  40                  45

Glu Asp Ala Ser Gly Tyr Leu Thr Ser Ser Trp Leu Thr Leu Phe Val
    50                  55                  60

Pro Ser Val Tyr Thr Gly Val Phe Val Val Ser Leu Pro
65                  70                  75

(2) INFORMATION FOR SEQ ID NO:4:

(i) SEQUENCE CHARACTERISTICS:
        (A) LENGTH: 10 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:4:

Ser Phe Leu Leu Arg Asn Pro Asn Asp Lys
1               5                   10

(2) INFORMATION FOR SEQ ID NO:5:

(i) SEQUENCE CHARACTERISTICS:
        (A) LENGTH: 14 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:5:

Ser Phe Leu Leu Arg Asn Pro Asn Asp Lys Tyr Glu Pro Phe
1               5                   10
```